(12) United States Patent
Albayrak

(10) Patent No.: US 8,802,148 B2
(45) Date of Patent: Aug. 12, 2014

(54) MICROPARTICLES AND METHOD FOR THEIR PRODUCTION

(75) Inventor: Celal Albayrak, Berlin (DE)

(73) Assignee: Alrise Biosystems GmbH, Berlin (DE)

( * ) Notice: Subject to any disclaimer, the term of this patent is extended or adjusted under 35 U.S.C. 154(b) by 1606 days.

(21) Appl. No.: 10/506,952

(22) PCT Filed: Mar. 14, 2003

(86) PCT No.: PCT/US03/07954
§ 371 (c)(1),
(2), (4) Date: Sep. 8, 2004

(87) PCT Pub. No.: WO03/077887
PCT Pub. Date: Sep. 25, 2003

(65) Prior Publication Data
US 2005/0106257 A1    May 19, 2005

(30) Foreign Application Priority Data

Mar. 15, 2002  (EP) .................................. 02005393

(51) Int. Cl.
*A61K 9/14* (2006.01)
*A61K 9/16* (2006.01)
*A61K 9/51* (2006.01)
*A61K 38/00* (2006.01)

(52) U.S. Cl.
USPC .......................................... 424/489; 514/1.1

(58) Field of Classification Search
USPC ....................................................... 424/489
See application file for complete search history.

(56) References Cited

U.S. PATENT DOCUMENTS

| | | | |
|---|---|---|---|
| 5,858,531 A * | 1/1999 | Chenite et al. | 428/402 |
| 5,869,103 A * | 2/1999 | Yeh et al. | 424/501 |
| 5,889,110 A * | 3/1999 | Hutchinson | 525/54.1 |
| 6,106,807 A | 8/2000 | Albayrak et al. | |
| 6,207,135 B1 | 3/2001 | Rössling et al. | |
| 6,294,204 B1 | 9/2001 | Rössling et al. | |
| 6,468,506 B1 | 10/2002 | Rössling et al. | |
| 6,572,894 B2 | 6/2003 | Rössling et al. | |
| 6,899,898 B2 | 5/2005 | Albayrak | |
| 7,081,489 B2 * | 7/2006 | Chen et al. | 523/200 |
| 2001/0033868 A1 | 10/2001 | Rössling et al. | |
| 2001/0038823 A1 | 11/2001 | Rössling et al. | |
| 2002/0192294 A1 | 12/2002 | Albayrak | |
| 2003/0049320 A1 * | 3/2003 | Bhagwatwar et al. | 424/486 |
| 2003/0068381 A1 | 4/2003 | Albayrak | |
| 2004/0126900 A1 * | 7/2004 | Barry et al. | 436/523 |

FOREIGN PATENT DOCUMENTS

| | | | |
|---|---|---|---|
| EP | 0 442 671 | 8/1991 | |
| EP | 0 586 238 | 3/1994 | |
| EP | 1344520 B1 * | 3/2010 | A61K 9/16 |

OTHER PUBLICATIONS

Stainmesse et al. ("Formation of Stabilization of a biodegradable polymeric suspension of nanoparticles", Colloid Polym Sci 273:505-511 (1995)).*
Castellanos et al., "Encapsulation of bovine serum albumin in poly(lactide-co-glycolide) microspheres by the solid-in-oil-in-water technique," J. of Pharmacy and Pharmacology, 53:167-178, (2001).
Morita et al., "Applicability of various amphiphilic polymers to the modification of protein release kinetics from biodegradable reservoir-type microspheres," Eur. J. of Pharm. and Biopharm., 51(1):45-53, (2001).
Putney et al., "Improving protein therapeutics with sustained-release formulations," Nature Biotechnology, 16:153-157, (1998).
Sah, "Protein Behavior at the Water/Methylene Chloride Interface," J. of Pharm. Sci., 88(12):1320-1325, (1999).

* cited by examiner

*Primary Examiner* — Maury Audet
(74) *Attorney, Agent, or Firm* — Kagan Binder, PLLC

(57) ABSTRACT

The invention relates to nano- or microparticles containing an active substance embedded in a polymer matrix and to a method for their production, comprising the steps of: a) effecting precipitation of an active substance in a solution which comprises a polymer dissolved in an organic solvent to obtain a suspension of the active substance, b) mixing the obtained suspension with an aqueous surfactant solution and solidifying the polymer to obtain a suspension of nano- or microparticles which contain an active substance.

7 Claims, 1 Drawing Sheet

MICROPARTICLES AND METHOD FOR THEIR PRODUCTION

FIELD OF THE INVENTION

The invention relates to a method for the preparation of nano- or microparticles comprising peptides, proteins or other water-soluble or non-water soluble bioactive substances and to particles provided according to this method.

BACKGROUND OF THE INVENTION

Following the rapid developments in biotechnology and genetic engineering within the last years, a large number of proteins and peptides of potential therapeutic use has been made available. However, the delivery of protein and peptide pharmaceuticals to patients is not easy to accomplish, largely due to their inherent physical and chemical instability. Upon oral administration to a patient, they undergo degradation due to hydrolysis in the acidic environment of the stomach, so that their activity in the gastrointestinal tract is significantly reduced. A relatively fast inactivation can also be observed after parenteral, in particular intravenous presentation which is due to the short half-life of many active substances. As a consequence, repeated high dosages of these compounds may be required in spite of their high pharmacological activity, which represents a significant burden for the patient. Compliance problems are furthermore obviated if the number of dosages can be reduced.

As suitable formulations overcoming the above-mentioned drawbacks, sustained release systems in the form of microspheres are known which control the release of the active substance by incorporating it in a shell or a matrix of a biodegradable polymer. Such formulations are most commonly provided via formation of microspheres by the "water-in-oil-in-water" (W/O/W) technique (e.g as disclosed in EP-A-442 671). However, it has become increasingly apparent that the protein solutions emulsified in the oil phase suffer from degradation due to denaturation of the protein structures at the water/oil interface during the preparation of the capsules. Furthermore, the influence of shear forces during emulsification may also contribute to a loss of active material.

In view of these problems, encapsulation strategies have been developed that try to minimize the exposure of hydrated proteins to physical stress factors, based on the finding that proteins in a crystalline or amorphous form are less susceptible to denaturation. Methods using the increased stability of proteins in their solid state have been published, e.g., by T. Morita et al., Eur. J. Pharm. Sci. 88 (1999) 45-53 or I. J. Castellanos et al., J. Pharm. Pharmacol., 53 (2001) 167-178. According to these "solid-in-oil-in-water" (S/O/W) techniques, proteins are suspended in an organic solution of the biodegradable polymer, followed by emulsification of the suspension in an aqueous solution and formation of solid microspheres via removal of the organic solvent. However, the S/O/W-technique as applied therein requires solutions of the active substance to be pretreated by micronization, spray drying or lyophilisation in order to obtain a powder suitable for being suspended in the polymer solution. Moreover, the flexibility of these methods with respect to an optimization of release properties of the final formulation is impaired, since the range for selective variations of particle size within these powders is frequently restricted by the type of apparatus used for their provision.

As a consequence, there is still a need for methods for the encapsulation of sensitive active substances which, while avoiding as far as possible complicated and time consuming process steps, allow the encapsulation of the active substances at a high efficiency and on an industrial scale. Moreover, the method should ensure control of release kinetics of the active substances, and, at the same time, allow the adaptation of these kinetics to different types of active substances and different therapeutical applications. It is finally also an object to overcome compliance problems which are especially encountered with elder patients.

SUMMARY OF THE INVENTION

Figure 1:
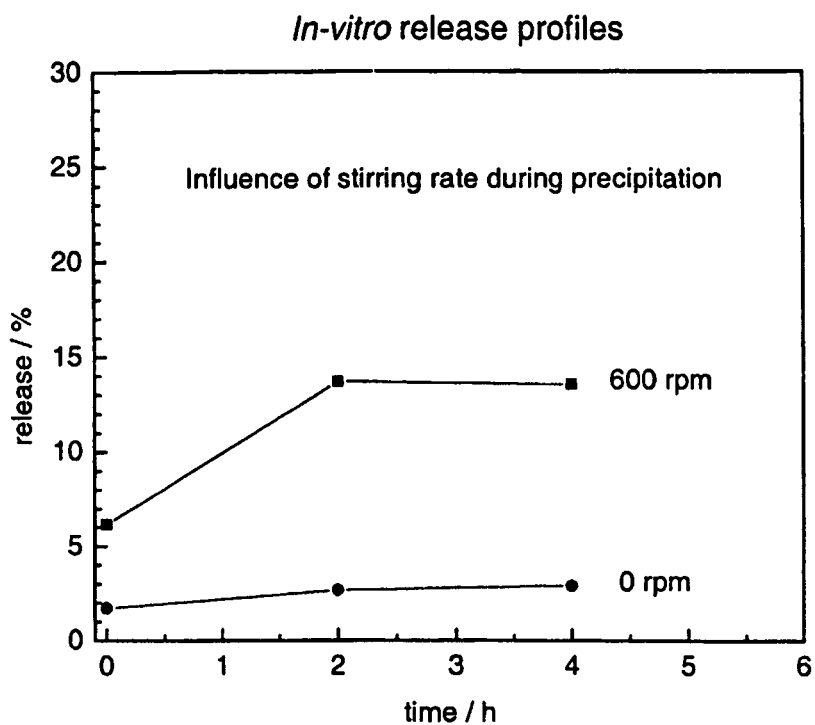
FIG. 1 depicts in-vitro release profiles of microparticles according to the invention.

The above aim has now been realized by means of a new method for the provision of drug loaded nano- or microparticles which may be referred to as an in-situ-precipitation method.

According to this method, active substances are embedded or encapsulated in a polymer matrix by the steps of
a) effecting precipitation of an active substance in a solution which comprises a polymer dissolved in an organic solvent to obtain a suspension of the active substance,
b) mixing the obtained suspension with an aqueous surfactant solution and solidifying the polymer to obtain a suspension of nano- or microparticles which contain an active substance.

As used herein, the terms "nanoparticles" or "miroparticles" include nano- and microspheres as well as nano- and microsponges.

This method can, for example, be advantageously used with proteins and peptides as active substances. If they are emulsified in the form of a solution, these bioactive compounds are liable to denaturation at the W/O interface (H. Sah, J. Pharm. Sci. 88 (1999) 1320-1325) and are particularly sensitive to shear forces. Such disadvantages are not encountered with the suspensions used in the method of the present invention.

Polymers or Copolymers suitable for formation of the polymer matrix should be degradable under the physiological conditions to which they are exposed after administration of the active-substances containing particles to the patient, a property which is often referred to as biodegradability. It should be understood that the mentioned polymers or copolymers should be biocompatible, i.e. they should not give rise to significant side effects in the patient's organism.

A convenient method for carrying out step a) above starts from a solution of the active substance in water or an organic solvent which is mixed with the solution of the polymer in an organic solvent. In a particularly preferred embodiment, the active substance is dissolved in a smaller amount of a first solvent L1. The polymer solution is prepared with the help of a larger amount of a second organic solvent L2 which dissolves the polymer, but is a non-solvent (anti-solvent) for the active substance. Then, L1 and L2 including the substances dissolved therein are combined. Upon combination of L1 and L2, precipitation of the active substance, which is insoluble in L2, is effected to yield a suspension of the active substance in the polymer solution. Preferably, the solvents L1 and L2 should be fully or partially miscible with each other for this purpose. Since an excess of the organic solvent L2 over L1 is used in this preferred embodiment, the liquid phase comprising the dissolved polymer together with the suspended active substance is referred to as an organic phase herein, irrespective of the fact that L1 may also be water.

From the suspension obtained in step a), the desired drug loaded nano- or microparticles are preferably formed via addition of an aqueous surfactant solution to the suspension of the active substance. This addition results in a phase transition from the organic phase as continuous phase to the aqueous phase as continuous phase. If the organic solvent for the polymer is chosen to be partially water soluble, immediate diffusion of the organic solvent from the discontinuous phase to the continuous phase results in the solidification of the polymer to form a matrix wherein the active substance is embedded. Thus, a suspension of the drug loaded nano- or microparticles is formed.

Alternatively, the desired drug loaded nano- or microparticles may be formed from the suspension obtained in step a) above via a conventional S/O/W process, i.e. by adding the suspension to an aqueous surfactant solution to form an emulsion comprising the organic polymer solution as a discontinuous phase wherein the active substance is suspended. The organic solvent is subsequently removed from the discontinuous phase, e.g. via application of reduced pressure, to effect the solidification of the polymer and to yield a suspension of the drug loaded nano- or microparticles. In this case, organic solvents may be used for the formation of the polymer solution of step a) above which are not or only little soluble in water.

The drug loaded polymer nano- or microparticles obtainable from the method according to the invention are characterized by a highly homogeneous size distribution of the particulate active substance embedded in the polymer matrix. More than 50, preferably more than 60, 70, 80 or even 90% of the drug loaded particles have the morphological structure of nano- or microspheres or nano- or microsponges.

Moreover, the average particle size of the active substance particles contained in the nano- or microparticles may be varied over a wide range such as from 10 nm to 500 µm, depending on the conditions applied during precipitation. Thus, if required, the active substance particles within the polymer matrix may exhibit an average particle diameter in the nm range, such as below 1000, 500, 100, 50, or even below 10 nm. Such small particle sizes are, e.g., of interest for particles for intravenous administration, which should not exceed an overall diameter of a few micrometers.

In the following, the invention shall be explained in more detail by reference to further preferred embodiments thereof.

Active substances or drugs which may be used for the purpose of the present invention are preferably those which are likely to suffer from degradation if processed in an aqueous solution. As stated above, the process of the invention is particularly suitable for the encapsulation of sensitive proteins and peptides such as hormones, growth factors, enzymes, antibodies, interleukines, lysozyme, interferones, fibronectins, peptide drugs, protein drugs, desensitizing agents, antigens, vaccines, anti-infectives, antibiotics, antimicrobials, antiallergenics, steroidal anti-inflammatory agents, decongestants, miotics, anti-cholinergics, sympathomimetics, sedatives, hypnotics, psychic energizers, tranquilizers, androgenic steroids, estrogens, progestational agents, humoral agents, prostaglandins, analgesics, antispasmodics, antimalarials, antihistamins, cardioactive agents, non-steroidal anti-inflammatory agents, antiparkinsonian agents, antihypersensitive agents, β-adrenergic blocking agents, nutritional agents, benzophenanthridine alkaloids, calcitonin, erythropoietin (EPO), cyclosporine, granulocyte colony stimulating factor (GCSF) granulocyte macrophage colony stimulating factor (GMCSF), growth hormones including human growth hormone (HGH), and growth hormone releasing hormone (GHRH), luteinizing hormone releasing hormone (LHRH) and LHRH analogues, insulin, somatostatin, somatostatin analogs including octreotide, vasopressin and its analogs, follicle stimulating hormone (FSH), and insulin-like growth factor under mild conditions.

Active substances suitable for the purpose of the present invention may be encapsulated into nano- or microparticles alone or in combinations of two or more of them.

Polymers or Copolymers which can be used as a matrix in the nano- or microparticles of the present invention include polyamides, polyanhydrides, polyester, polyorthoester, polyacetates, polylactones or polyorthocarbonate. Preferred among such biodegradable polymers are polyesters of hydroxycarboxylic acids in general, block-copolymers of hydroxycarboxylic acid polyesters with (C2-C4) polyalkyleneglycol, polyglycolides (PGA) and copolymers of glycolides such as glycolide/lactide-copolymers (PLLA/PGA) or glycolide/trimethylenecarbonate-copolymers (PGA/TMC); L-polylactides (PLA) and stereocopolymers of polylactides such as poly-L-lactide (PLLA), poly-DL-lactide-copolymers and L-lactide/DL-lactide-copolymers; copolymers of PLA such as lactide/tetramethylglycolide-copolymers; lactide/δ-valerolactone-copolymers and lactide/e-caprolactone-copolymers; poly-β-hydroxybutyrate (PHBA), PHBA/β-hydroxyvalerate-copolymers (PHBA/HVA), poly-β-hydroxypropionate (PHPA), poly-p-dioxanone (PDS), poly-δ-valerolactone, poly-ε-caprolactone, polyaminoacids, hydrophobized polysaccharides, hydrophobized hyaluronic acid, hydrophobized dextranes or self-organizing hydrophobized amylopectine, chitosane, hyaluronic acid or hydrophobized proteins. Also, block copolymers of polyesters and linear or star-polyethyleneglycol (PEG), such as AB-block copolymers of PLGA and PEG, ABA-triblock copolymers of PEG-PLGA-PEG, S(3)-PEG-PLGA-S(3) block copolymers and S(4)-PEG-PLGA block copolymers may be used.

Particularly preferred polymers are poly(DL-lactide-coglycolides). They are, for example, commercially available under the trade name of Resomer® by Böhringer Ingelheim (Germany). Typical representatives thereof are Resomer® L-104, L-206, L-207, L-208, L-209, L-210, L214, R-104, R-202, R-203, R-206, R-207, R-208, G-110, G-205, LR-909, RG-502, RG-502H, RG-503, RG-503H, RG-504, RG-504H, RG-505, RG-505H, RG-506, RG-508, RG-752, RG-755, RG-756 and RG-858.

Depending on the type of polymer as well as on the type of active substance used, the weight ratio between both used in the particles according to the invention may vary. However, it is frequently chosen so as to obtain particles with a content (or payload) of the active substance ranging from 0.1 to 40 wt %, preferably 1 to 20 wt % or 1 to 10 wt %, based on the total weight of the active substance and the polymer.

As set out above, it is a convenient way to accomplish precipitation of the active substance in the polymer solution via combination of a smaller amount of a first solvent L1 which dissolves the active substance with a larger amount of a second organic solvent L2 which dissolves the polymer. If L2 is suitably chosen as a non-solvent (anti-solvent) for the active substance, the diffusion of L1 into the polymer phase will then lead to the in situ precipitation of the particulate active substance. In order to allow this process step to be carried out effectively, L1 and L2 should be miscible with each other. Full (i.e. 100%) miscibility of L1 and L2 ensures a high yield of the precipitation. However, since L2 is usually used in excess, the same good result can be achieved if L1 and L2 are only partially miscible as long as the amount of L1 is sufficient to dissolve all of L2.

Generally, the relative amounts of solvents L1 and L2 are determined by the solubility of the active substance and the polymer, respectively, as well as by the desired weight ratio of the active substance and the polymer in the final drug loaded particles. Usually, the ratio of L1 to L2 ranges between 1:2 to 1:1000, preferably 1:2 to 1:100, 1:50 or 1:20 (vol/vol).

It is advantageous to use concentrated solutions of the active substance in L1. While the active substance must not be soluble in L2, the polymer should preferably be soluble in both L1 and L2.

In order to better control the precipitation of the crystalline particles, it is preferred to combine the solutions by adding L1 to L2 (although the vice-versa method should not be excluded). For example, L1 can be added dropwise or by slowly pouring it into L2. During the addition, L2 is preferably agitated, e.g. by means of a mechanical stirrer, such as a magnetic stirrer or a dispersing device.

According to a preferred embodiment of the method of the present invention explained above, drug loaded nano- and microparticles are formed by adding an aqueous surfactant solution to the suspension of step a) to induce a phase transition from the organic phase as a continuous phase to the aqueous phase as a continuous phase with simultaneous solidification of the polymer. In this particular embodiment, a defined volume of an aqueous solution or buffer solution containing a surfactant or surfactant mixture is added to the organic phase comprising the dissolved polymer and the active substance in the form of a suspension. Preferably, the organic phase is agitated during the addition.

Following this method, the organic solvent(s) used for the preparation of the polymer solution must be chosen to be partially soluble in the aqueous surfactant solution. Preferably, the solubility of the solvent(s) in water or buffered solutions should range between 1.5 and 40% (w/w), more preferred are values between 1.5 to 30%. When the aqueous surfactant solution is added under stirring to the suspension obtained in step a) above, the organic solvent(s) is (are) dissolved in water. As a result, the polymer is solidified and a suspension of the desired nano- or microparticles comprising the solid active substance distributed (embedded) in a solid polymer is formed in the aqueous solution.

Suitable organic solvents for the polymer may be selected based on their miscibility with the aqueous surfactant solution. Suitable parameters to support this selection are the solubility parameters ($\delta(\text{cal/cm}^3)^{1/2}$) of the polymer solvent and the aqueous surfactant solution.

Preferably, these values are chosen to obey the following equation:

$$\delta(\text{polymer solvent}) - \delta(\text{aqueous surfactant solution}) \leq 0,$$

and particularly preferred are values of the above equation within the range 0 to $-15$ $(\text{cal/cm}^3)^{1/2}$.

Solubility parameters of suitable solvents which may be used as solvents for the preparation of the polymer solution of step a) above are given in the following table. Suitable solvents (L1) and non-solvents (L2) to be used according to the preferred embodiment of the present invention may also be chosen from this non-exclusive list depending on the active substance to be encapsulated. Water has a solubility parameter $\delta$ of 23.41 $(\text{cal/cm}^3)^{1/2}$.

| Solvent | Solubility Parameter $\delta$/ $(\text{cal} \cdot \text{cm}^{-3})^{1/2}$ |
| --- | --- |
| methyl acetate | 9.65 |
| ethyl acetate | 8.90 |
| propyl acetate | 8.8 |
| methyl formate | 10.2 |
| isobutyl acetate | 8.3 |
| butyl acetate | 8.5 |
| iIsopropyl acetate | 8.4 |
| propyl formate | 9.2 |
| dimethyl sulfoxide | 12.0 |
| ethyl formate | 9.4 |
| methyl-pyrrolidon-2 (N) | 11.3 |
| tetrahydrofuran | 9.1 |
| methyl ethyl ketone | 9.29 |
| acetone | 9.82 |
| acetonitrile | 11.95 |
| dioxane | 10.02 |
| THF | 9.49 |
| DMSO | 13.04 |

Values for the solubility parameters of solvents are given, e.g. in the "Polymer Handbook" (J. Bransrup, E. H. Immergut, E. A. Grulke, Wiley Interscience 1999).

For the purpose of the selection of a suitable solvent for the polymer, the influence of the optional second solvent used for the dissolution of the active substance (such as L1 in the preferred embodiment) can be disregarded, since its volume is significantly smaller than that of the polymer solvent.

In addition to the solubility parameters, the volume fraction of the suspension and the aqueous surfactant solution combined in step b) above are preferably selected in order to ensure that a suspension of the drug loaded nano- or microparticles is formed immediately upon combining the organic phase with the aqueous surfactant solution. Accordingly, the volume ratio of the organic phase and the aqueous surfactant solution is usually within the range of 1:1.5-1:30, preferably 1:2-1:20. In a particularly preferred embodiment, the volume of the continuous aqueous surfactant phase required for the phase transition is calculated under the assumption that the polymer microparticles suspended in the continuous surfactant phase occupy the cavities in a "body centered cubic" or "face centered cubic" or "hexagonal close pack" arrangement. In this case, the volume fraction of the aqueous surfactant phase is greater than approximately 60%, preferably between 65 and 80%, and most preferably between 68% and 74%, based on the combined aqueous and organic phases. Thus, the required volume of the aqueous surfactant solution is usually smaller than it is in conventional encapsulation methods where non-polar organic solvents are used which are non-miscible with water.

Exemplary solvents which may be used for the preparation of the polymer solution and, if desired, for the preparation of a solution of the active substance prior to the precipitation step are alkyl acetates such as methyl acetate, ethyl acetate, propyl acetate, isopropyl acetate, isobutyl acetate, t-butyl acetate, n-butyl acetate; alkyl formates such as methyl formate, ethyl formate, propyl formate, isopropyl formate, n-butyl formate, isobutyl formate, t-butyl formate, alkyl lactates such as methyl lactate, ethyl lactate, glycofurol, PEG-100, PEG-200, PEG-300, PEG-400, triacetin, triethyl citrate, DMSO, THF, aceton, N-metyl-2-pyrrolidone, 1-methyl-2-pyrrolidone, dimethylforamide, metylethylketone, methylisobutylketone, acetonitrile, diethylcarbonate, 3-metyl-1-butanol, 2-metyl-1-propanol, ethanol, propyleneglycol, glycerol, polyethleneglycol, dimethylcetimide, propylencarbonat, and caprolactam.

The solvents L1 and L2 to be used in the preferred precipitation method of the present invention may equally be selected from the above non-exhaustive list. Suitable combinations of L1 and L2 are best selected depending on the type of active substance which is to be encapsulated. In this context, it must be kept in mind that the active substance must be soluble in L1 but not in L2 and that L1 and L2 should be fully or partially miscible. Water or an aqueous solution as a solvent may only be used as L1. In this case, the organic solvent L2 should preferably have a sufficiently high solubility in water, to allow all of L1 to be dissolved in D2. The following table provides some exemplary solubility values for organic solvents in water at 20-25° C. to support the choice of a solvent to provide the polymer solution in step a) above.

| Solvent | Solubility in water (w/w) [%] |
|---|---|
| methyl acetate | 22.8 |
| ethyl acetate | 7.43 |
| propyl acetate | 1.67 |
| isopropyl acetate | 3.09 |
| methyl formate | 30 |
| ethyl formate | 8.4 |
| propyl formate | 2.82 |
| methyl-ethyl-ketone | 23 |

Suitable surfactants to provide the aqueous surfactant solution used in the present invention are those of the cationic, anionic, nonionic or zwitterionic type, such as alkylethers of polyethyleneglycol, esters of carbohydrates such as saccharose, polysorbates (Tween®, Span®), alkali salts of fatty acids such as sodium oleate, polyoxylated fatty acids ethers (Brij®), glycosides of fatty alcohols, polyvinyl pyrrolidone (PVP), polyvinyl alcohol (PVA), poloxamer®, poloxamine®, Chaps, Chapso, decyl-β-D-glycopyranoside, decyl-β-D-maltopyranoside, dodecyl-β-D-maltopyranoside, sucrose esters (Ryoto sugar esters Tokyo, Sisterna®, Netherlands, SDS, cetyltrimethylammonium bromide, cetylpyridinium chloride, didodecyldimethylammonium bromide, choltate sodium, deoxychlote sodium, glycocholte sodium or Triton-X-100, all of which may be used alone or in mixtures of two or more thereof in concentrations ranging preferably between 1-10% (w/w).

Moreover, buffers such as tris (hydroxymethyl) aminomethane, phosphates or citrate may be present in the aqueous solution, and they are generally used in concentrations of 5 mmol/l to 300 mmol/l.

Once the solidification of the polymer in step b) of the method of the invention is completed, the organic solvent or solvent mixture can be removed via conventional methods, such as application of a reduced pressure and/or a flow of air or nitrogen, filtration or extraction.

After their recovery from the aqueous suspension, the nano- or microparticles may be washed with water, optionally repeatedly, to remove remaining solvent and surfactant as well as traces of active agent which may be present on their surface. Alternatively, the particles may be subjected to cross-flow-filtration for this purpose.

In order to increase their stability, the drug loaded nano- or microparticles may be lyophilized, optionally together with a cryoprotectant such as a sugar, sugar alcohol or a polyvinyl pyrrolidone derivative.

The present invention allows the provision of nano- and microparticles which are specifically designed to meet the requirements of their respective applications. In this respect, it is one of the benefits of the method disclosed herein is that it enables or at least facilitates changes in the particle performance without the necessity for significant changes in the used equipment. For example, the size of the particles of the active substance embedded within the polymer, and as a result thereof, the release profile of this substance, can be varied by applying specifically adopted stirring speeds during precipitation of the active substance. If a high speed stirrer or mixer is used (such as a dispersing device), the aggregates of the active substance will be small. A reduction of the stirring speed will, on the other hand, lead to particles of the active substance with a large average diameter. Due to their lower surface/volume-ratio, such larger particles will show a release rate which is reduced compared to that of small particles. Consequently, one can prepare a wide range of particle sizes by combining the above-mentioned measures in the desired direction.

Moreover, the in situ precipitation step (the previously mentioned step a)) yields particles of the active substance which are very homogeneous in their appearance and show a narrow particle size distribution. As a consequence, the initial burst release of the active substance, which represents a common problem of controlled-release formulations, can be reduced below 20 10 or even 5 wt % of the overall payload of the nano- or microparticles.

The following examples are meant to illustrate the present invention without restricting it thereto.

EXAMPLE 1

3.0 g Resomer® 756 are dissolved in 11.5 ml ethyl formate and transferred to a double-walled steel vessel (inside height of 11.0 cm, inside diameter of 4 cm) Subsequently, 2.7 ml DMSO solution, containing 100 mg goserelin acetate, are slowly dripped under stirring (600 rpm) with a mechanical stirrer (Dispermat FT.VMA-Getzmann GmbH, 2 cm dissolver disc) to the polymer solution. The resulting suspension is stirred at 6000 rpm for 6 minutes, and subsequently 50 ml of an aqueous, tris-buffered solution (pH=7.4) containing 2 g Pluronic® F-68, are added as a continuous phase. After five minutes of stirring, the suspension of microparticles is transferred to a two-neck flask and stirred with a magnetic stirrer. Then, the solvent is removed at ambient temperature via application of vacuum or via extraction with water.

From the microparticles, excess surfactant and non-encapsulated active agent are removed via centrifuging or filtration, they are repeatedly washed with water and lyophilized under addition of a cryoprotectant.

The lyophilisate, resuspended in water or an aqueous solution contains microspheres with a content of goserelin of 2.80% (mass of goserelin*100/(mass of polymer+mass of goserelin)=degree of loading) and with a diameter of 1-40 µm.

EXAMPLE 2

3.0 g Resomer® 756 are dissolved in 11.5 ml ethyl formate and transferred to a double-walled steel vessel (inside height of 11.0 cm, inside diameter of 4 cm) Subsequently, 2.7 ml NMP solution, containing 100 mg goserelin acetate, are slowly dripped under stirring (600 rpm) with a mechanical stirrer (Dispermat FT.VMA-Getzmann GmbH, 2 cm dissolver disc) to the polymer solution. The resulting suspension is stirred at 6000 rpm for 6 minutes, and subsequently 50 ml of an aqueous, tris-buffered solution (pH=7.4) containing 2 g Pluronic® F-68, are added as a continuous phase. After five minutes of stirring, the suspension of microparticles is transferred to a two-neck flask and stirred with a magnetic stirrer. Then, the solvent is removed at ambient temperature via application of vacuum or via extraction with water.

From the microparticles, excess surfactant and non-encapsulated active agent are removed via centrifuging or filtration, they are repeatedly washed with water and lyophilized under addition of a cryoprotectant.

The lyophilisate, resuspended in water or an aqueous solution contains microspheres with a content of goserelin of 2.78% (mass of goserelin*100/(mass of polymer+mass of goserelin)=degree of loading) and with a diameter of 1-40 µm.

EXAMPLE 3

3.0 g Resomer® 756 are dissolved in 11.5 ml ethyl formate and transferred to a double-walled steel vessel (inside height of 11.0 cm, inside diameter of 4 cm) Subsequently, 2.7 ml Peg-200 solution, containing 100 mg goserelin acetate, are slowly dripped under stirring (600 rpm) with a mechanical stirrer (Dispermat FT.VMA-Getzmann GmbH, 2 cm dissolver disc) to the polymer solution. The resulting suspension is stirred at 6000 rpm for 6 minutes, and subsequently 50 ml of an aqueous, tris-buffered solution (pH=7.4) containing 2 g Pluronic® F-68, are added as a continuous phase. After five minutes of stirring, the suspension of microparticles is transferred to a two-neck flask and stirred with a magnetic stirrer. Then, the solvent is removed at ambient temperature via application of vacuum or via extraction with water.

From the microparticles, excess surfactant and non-encapsulated active agent are removed via centrifuging or filtration, they are repeatedly washed with water and lyophilized under addition of a cryoprotectant.

The lyophilisate, resuspended in water or an aqueous solution contains microspheres with a content of goserelin of 2.88% (mass of goserelin*100/(mass of polymer+mass of goserelin)=degree of loading) and with a diameter of 1-40 µm.

EXAMPLE 4

3.0 g Resomer® 756 are dissolved in 11.5 ml ethyl formate and transferred to a double-walled steel vessel (inside height of 11.0 cm, inside diameter of 4 cm) Subsequently, 2.7 ml 2-Pyrrolidone solution, containing 100 mg goserelin acetate, are slowly dripped under stirring (600 rpm) with a mechanical stirrer (Dispermat FT.VMA-Getzmann GmbH, 2 cm dissolver disc) to the polymer solution. The resulting suspension is stirred at 6000 rpm for 6 minutes, and subsequently 50 ml of an aqueous, tris-buffered solution (pH=7.4) containing 2 g Pluronic® F-68, are added as a continuous phase. After five minutes of stirring, the suspension of microparticles is transferred to a two-neck flask and stirred with a magnetic stirrer. Then, the solvent is removed at ambient temperature via application of vacuum or via extraction with water.

From the microparticles, excess surfactant and non-encapsulated active agent are removed via centrifuging or filtration, they are repeatedly washed with water and lyophilized under addition of a cryoprotectant.

The lyophilisate, resuspended in water or an aqueous solution contains microspheres with a content of goserelin of 2.90% (mass of goserelin*100/(mass of polymer+mass of goserelin)=degree of loading) and with a diameter of 1-40 µm.

EXAMPLE 5

3.0 g Resomer® 756 are dissolved in 11.5 ml ethyl formate and transferred to a double-walled steel vessel (inside height of 11.0 cm, inside diameter of 4 cm) Subsequently, 2.7 ml NMP solution, containing 100 mg goserelin acetate, are slowly dripped without stirring to the polymer solution. The resulting suspension is stirred with a mechanical stirrer (Dispermat FT.VMA-Getzmann GmbH, 2 cm dissolver disc) at 6000 rpm for 6 minutes, and subsequently 50 ml of an aqueous, tris-buffered solution (pH=7.4) containing 2 g Pluronic® F-68, are added as a continuous phase. After five minutes of stirring, the suspension of microparticles is transferred to a two-neck flask and stirred with a magnetic stirrer. Then, the solvent is removed at ambient temperature via application of vacuum or via extraction with water.

From the microparticles, excess surfactant and non-encapsulated active agent are removed via centrifuging or filtration, they are repeatedly washed with water and lyophilized under addition of a cryoprotectant.

The lyophilisate, resuspended in water or an aqueous solution contains microspheres with a content of goserelin of 2.94% (mass of goserelin*100/(mass of polymer+mass of goserelin)=degree of loading) and with a diameter of 140 µm.

EXAMPLE 6

3.0 g Resomer® 756 are dissolved in 11.5 ml ethyl acetate and transferred to a double-walled steel vessel (inner height of 11.0 cm, inside diameter of 4 cm). Subsequently, 2.7 ml NMP solution containing 75 mg goserelin acetate are slowly dripped to the polymer solution under stirring (600 rpm) with a mechanical stirrer (Dispermat FT.VMA-Getzmann GmbH, 2 cm dissolver disc). The resulting suspension is stirred at 6000 rpm for 6 minutes and subsequently 50 ml of an aqueous, tris-buffered solution (50 mmol, pH=7.2) containing 2 g Pluronic® F-68 are added as a continuous phase. After five minutes of stirring the suspension of microparticles is transferred to a 500 ml two-neck flask and stirred with a magnetic stirrer. Then, the solvent is removed at ambient temperature via application of vacuum or via extraction with water.

From the microparticles, excess surfactant and non-encapsulated active agent are removed via centrifuging or filtration, they are repeatedly washed with water and lyophilized under addition of a cryoprotectant.

The lyophilisate, resuspended in water or an aqueous solution, contains microspheres with a content of goserelin of 2.09% (mass of goserelin*100/(mass of polymer+mass of goserelin)=degree of loading) and with a diameter of 140 µm.

EXAMPLE 7

3.0 g Resomer® 756 are dissolved in 11.5 ml isopropyl formate and transferred to a double-walled steel vessel (inner height of 11.0 cm, inside diameter of 4 cm). Subsequently, 2.7 ml 2-pyrrolidone solution containing 75 ml goserelin acetate are slowly dripped to the polymer solution under stirring (600 rpm) with a mechanical stirrer (Dispermat FT.VMA-Getzmann GmbH, 2 cm dissolver disc). The resulting suspension is stirred at 6000 rpm for 6 minutes and subsequently 50 ml of an aqueous, tris-buffered solution (50 mmol, pH=7.2) containing 2 g Pluronic® F-68 are added as a continuous phase. After five minutes of stirring, the suspension of microparticles is transferred to a 500 ml two-neck flask and stirred with a magnetic stirrer. Then, the solvent is removed at ambient temperature via application of vacuum or via extraction with water.

From the microparticles, excess surfactant and non-encapsulated active agent are removed via centrifuging or filtration, they are repeatedly washed with water and lyophilized under addition of a cryoprotectant.

EXAMPLE 8

3.0 g Resomer® 756 are dissolved in 11.5 ml ethyl formate and transferred to a double-walled steel vessel (inner height of 11.0 cm, inside diameter of 4 cm). Subsequently, 2.7 ml DMSO solution containing 75 mg eST (equine Samototropine) are slowly dripped to the polymer solution under stirring (600 rpm) with a mechanical stirrer (Dispermat FT.VMA-Getzmann GmbH, 2 cm dissolver disc). The resulting suspension is stirred at 6000 rpm for 6 minutes and subsequently 50 ml of an aqueous, tris-buffered solution (50 mmol, pH=7.2) containing 2 g Pluronic® F-68 are added as a continuous phase. After five minutes of stirring, the suspension of microparticles is transferred to a 500 ml two-neck flask and stirred with a magnetic stirrer. Then, the solvent is removed at ambient temperature via application of vacuum or via extraction with water.

From the microparticles, excess surfactant and non-encapsulated active agent are removed via centrifuging or filtration, they are repeatedly washed with water and lyophilized under addition of a cryoprotectant.

The lyophilisate, resuspended in water or an aqueous solution, contains microspheres with a content of goserelin of 2.08% (mass of goserelin*100/(mass of polymer+mass of goserelin)=degree of loading) and with a diameter of 1-40 μm.

EXAMPLE 9

3.0 g Resomer® 756 are dissolved in 11.5 ml ethyl formate and transferred to a double-walled steel vessel (inner height of 11.0 cm, inside diameter of 4 cm). Subsequently, 2.7 ml DMSO solution containing 75 mg insulin are slowly dripped to the polymer solution under stirring (600 rpm) with a mechanical stirrer (Dispermat FT.VMA-Getzmann GmbH, 2 cm dissolver disc). The resulting suspension is stirred at 6000 rpm for 6 minutes and subsequently 50 ml of an aqueous, tris-buffered solution (50 mmol, pH=7.2) containing 2 g Pluronic® F-68 are added as a continuous phase. After five minutes of stirring, the suspension of microparticles is transferred to a 500 ml two-neck flask and stirred with a magnetic stirrer. Then, the solvent is removed at ambient temperature via application of vacuum or via extraction with water.

From the microparticles, excess surfactant and non-encapsulated active agent are removed via centrifuging or filtration, they are repeatedly washed with water and lyophilized under addition of a cryoprotectant.

The lyophilisate, resuspended in water or an aqueous solution, contains microspheres with a content of goserelin of 2.08% (mass of goserelin*100/(mass of polymer+mass of goserelin)=degree of loading) and with a diameter of 1-40 μm.

EXAMPLE 10

In-Vitro Release Analysis

Approximately 20 mg of drug loaded microparticles were weighed into 10 ml vials and suspended in 5 ml of 10 mM PBS (pH=7.4) containing 0.1% Tween 20. The samples were shaken at 130 rpm on an orbital shaker at 37° C. After desired time elapsed 2 ml of suspension were removed and filtrated to separate release media from particles. Afterwards goserelin content in release media was measured.

In-vitro release profiles of examples 2 and 5 are shown in FIG. 1

EXAMPLE 11

Conductivity Measurements

Figure 2:
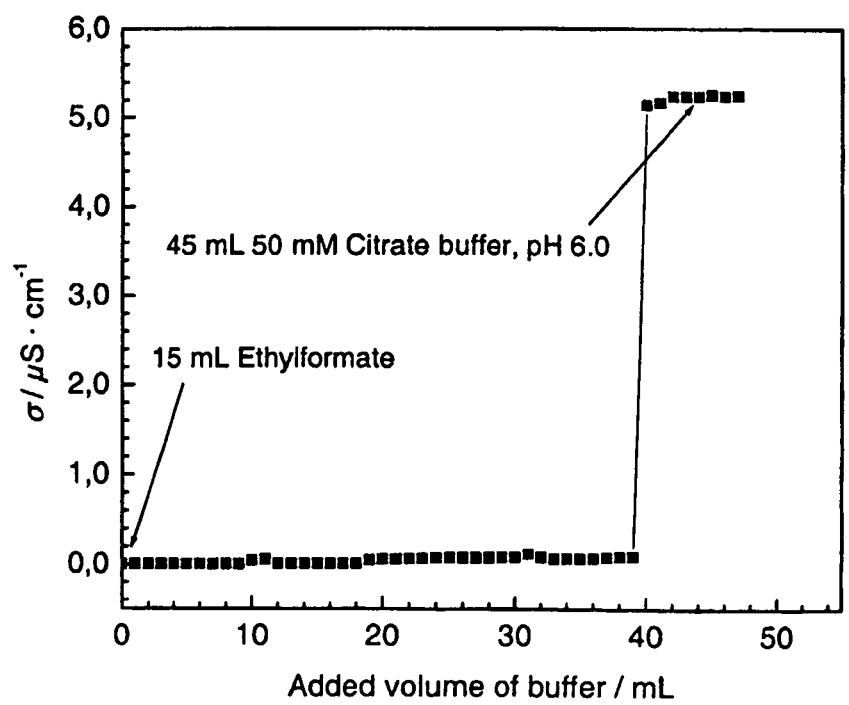
FIG. 2 depicts conductivity measurements to detect the phase transition according to the process of the invention.

In order to detect the phase transition from the organic phase as a continuos phase to the aqueous surfactant phase as a continuous phase during the addition of the latter to the suspension of the active substance obtained in an organic phase, the following conductivity measurement has been carried out in a model experiment. To 15 ml of ethyl formate, a citrate buffer solution was slowly added while the conductivity of the liquid phase was monitored. After the addition of approximately 40 ml of buffer solution, the phase transition occurred, leading to a remarkable increase of conductivity as shown in FIG. 2.

It is claimed:

1. A method for the preparation of microparticles containing an active substance embedded in a polymer matrix, comprising the steps of:
   a) combining a solution of an active substance dissolved in a smaller amount of a first solvent L1 selected from water or organic solvent with a solution of a polymer in a larger amount of a second organic solvent L2, said solvent L2 dissolving the polymer but being a non-solvent for the active substance, thereby effecting precipitation of the active substance in the combined solvent L1 and solvent L2 solution to obtain a suspension of the active substance having an organic phase as a continuous phase,
   b) mixing the combined solvent L1 and solvent L2 solution with an aqueous surfactant solution wherein L2 is partially soluble in the aqueous surfactant solution and the mixing results in a phase transition from having an organic continuous phase to having an aqueous continuous phase, thereby solidifying the polymer, forming a matrix and embedding the active substance within the polymer to obtain a suspension of microparticles; wherein said active substance is selected from the group of compounds that are sensitive to denaturation, degradation in aqueous solutions or shear forces.

2. The method according to claim 1, wherein L1 and L2 are fully or partially miscible.

3. The method of claim 1, wherein L1 and L2 are combined under stirring.

4. The method of claim 1, wherein the solvent L1, when an organic solvent, and/or the solvent L2 organic solvent(s) used in the method is (are) partially soluble in water.

5. The method of claim 1, wherein the volume fraction of the aqueous surfactant solution of step b) ranges between 60 and 80% of the total composition after mixing with the obtained suspension of step a).

6. The method of claim 1, wherein the active substance is a protein or a peptide.

7. The method of claim 1 wherein the polymer is a poly (DL-lactide-co-glycolide).

* * * * *